(12) United States Patent
Caserta et al.

(10) Patent No.: US 8,511,580 B2
(45) Date of Patent: Aug. 20, 2013

(54) CONTAINER OF ACTIVE SUBSTANCES

(75) Inventors: Andrea Caserta, Barcelona (ES); Ruben Garcia Fabrega, Barcelona (ES); Jose Antonio Muñoz Martinez, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 1587 days.

(21) Appl. No.: 11/072,299

(22) Filed: Mar. 7, 2005

(65) Prior Publication Data

US 2006/0032937 A1    Feb. 16, 2006

(30) Foreign Application Priority Data

Aug. 13, 2004   (WO) ..................  PCT/ES04/00375

(51) Int. Cl.
    *A24F 25/00*    (2006.01)
(52) U.S. Cl.
    USPC .............................................. 239/45; 239/44
(58) Field of Classification Search
    USPC ................... 239/34, 35, 41–43, 47, 51.5, 53, 239/55, 56, 57, 302, 45
    See application file for complete search history.

(56) References Cited

U.S. PATENT DOCUMENTS

| | | | |
|---|---|---|---|
| 4,165,835 A * | 8/1979 | Dearling | 239/51.5 |
| 4,356,969 A | 11/1982 | Obermayer et al. | |
| 4,753,389 A * | 6/1988 | Davis | 239/6 |
| 5,000,383 A * | 3/1991 | van der Heijden | 239/47 |
| 5,121,881 A * | 6/1992 | Lembeck | 239/44 |
| 5,234,162 A * | 8/1993 | Sullivan | 239/56 |
| 5,716,000 A | 2/1998 | Fox | |
| 5,718,000 A | 2/1998 | Ost et al. | |
| 5,749,519 A * | 5/1998 | Miller | 239/44 |
| 6,367,706 B1 * | 4/2002 | Putz | 239/6 |
| 6,555,069 B1 * | 4/2003 | Ferguson | 422/126 |
| 7,095,953 B2 | 8/2006 | Caserta et al. | |
| 2003/0089791 A1 | 5/2003 | Chen et al. | |

FOREIGN PATENT DOCUMENTS

| | | |
|---|---|---|
| EP | 1 240 907 A1 | 9/2002 |
| EP | 1579762 | 9/2005 |
| WO | WO 2004/049795 A1 | 6/2004 |

OTHER PUBLICATIONS

International Search Report dated Aug. 13, 2004, in PCT/ES 2004-000375.

* cited by examiner

*Primary Examiner* — Davis Hwu
(74) *Attorney, Agent, or Firm* — McDermott Will & Emery LLP

(57) ABSTRACT

Comprises a vessel (1) that houses the active liquid substance to be diffused, such as a fragrance, insecticide or other, through a breathable membrane (2) that closes the vessel (1) and comprises a porous part (3) placed near and parallel to the breathable membrane (2) in order to prevent the deformation of the membrane (2) when a vacuum is generated as the vessel (1) is emptied. The porous part (3) has a number of openings (4) through which passes the liquid to ensure its contact with the membrane (2) at all times for a homogenous evaporation and it occupies part of the volume of the vessel (1), absorbing the active substances, the non-volatile substances remaining in said porous part (3) after the vessel (1) has no more volatile components.

8 Claims, 3 Drawing Sheets

CONTAINER OF ACTIVE SUBSTANCES

OBJECT OF THE INVENTION

This invention relates to a container used to diffuse active substances such as fragrances, insecticides and others, stored in a liquid state and diffused in gaseous state through a breathable membrane.

The object of the invention is to dispose in the container in a suitable manner an element that prevents the deformation of the membrane when it is curved due to the vacuum produced when the liquid stored inside exits without the entry of air, as well as said element occupying a space inside the container that reduces part of the air chamber inside it while facilitating the passage of liquid to the membrane so that the latter is always in contact with the liquid for a homogenous diffusion.

BACKGROUND OF THE INVENTION

Diffusers of active substances used to diffuse fragrances, insecticides and others to the environment may incorporate a container vessel that houses the volatile substance, provided with a porous membrane that allows the vapour of said substance but not the liquid to pass.

A number of problems related to the manufacturing and operation of this type of device can be identified, as described below.

During the filling process, the liquid substance introduced in the container may splash the area of the container on which the membrane is soldered, producing a humidity that affects the quality of the weld. This means that the membrane may move, resulting in a loss of liquid.

To prevent splashes on the welding area, two containers are used with a smaller volume than foreseen, resulting in a large air chamber inside the container. This means that the user has the impression of purchasing an incomplete product, in which part of the liquid has been used.

Another solution to avoid the problem of undesired splashes is increasing the viscosity of the products to be evaporated, using very viscous gels or liquids with the problem that these products have a considerable non-volatile residue.

Another problem related to this type of devices relates to the fact that during the evaporation of the substance a vacuum is generated inside the container, as no air enters it. Thus, the membrane is sucked in causing it to bend inwards, generating tensions that may lead to its breakage at its area of attachment to the container.

In this situation the volume of the container is reduced as the membrane deforms, so that the consumer may observe an liquid level identical or even higher than the initial level when comparing it to the altered useful volume of the container. This means that it is not possible to appreciate a gradual evolution of its consumption.

In addition, during the evaporation the liquid level changes, so that the contact surface of the membrane and the liquid is reduced, resulting in a slower evaporation rate. The reduced evaporation rate along the product lifetime implies a depreciation of its functionality, the consumer noticing this significant loss of performance.

Another problem relates to the fact that membrane systems are only permeable to volatile substances, not to the remaining components that form part of the substance such as those used to modify its viscosity, protect its colour, antioxidants, colorants and others. These products remain in the container when the volatile liquid has evaporated completely, so that it is difficult for the end consumer to appreciate when its use has finished, as an unevaporated remainder is still observed inside the container.

DESCRIPTION OF THE INVENTION

The container of volatile substances that constitutes the object of this invention solves the problems described above by incorporating a porous inner rigid part behind the permeable membrane though which the volatile substance stored in a vessel constituting the container is diffused.

The porous inner part, which can for example be made of cellulose, porous plastic, ceramic or other materials, is placed parallel to and near the membrane, so that it can support the membrane and prevent its deformation when it bends due to the action of the vacuum generated as the liquid stored in the container exits.

The vessel incorporates a peripheral receptacle designed to facilitate housing the aforementioned porous part.

Also worthy of note is that the porous inner part has a number of openings that allow the liquid to pass toward the membrane at all times, so that the membrane is wet on its entire surface, determining a more homogenous and regular evaporation of the substance to the exterior at all times, without any difference between the beginning and the end.

The porous part occupies part of the volume that was previously occupied in other devices by the air chamber left in the filling process, so that the space of the vessel used to house the liquid appears nearly full. The capacity of the porous part to retain a greater or lesser amount of liquid is determined by the type of material and pore size selected.

The porosity of the material conforming the part allows housing the non-volatile part corresponding to the additional components of the substance, such as stabilisers, preservatives and colorants, so that when the container reaches the end of its useful life these components will be absorbed by the porous part and no liquid substance will be seen in the container, indicating the user in a clear manner that the container has reached the end of its life.

In addition, the porous part can prevent possible splashes that may land on the welding area while the vessel is being filled, by simple placing this part on said area to absorb the liquid. This eliminates any liquid contamination of this area, ensuring a correct seal of the membrane on the vessel.

The porous part also includes a mark, which may be a logo or any other image or text of interest from a marketing standpoint, visible through a transparent vessel.

DESCRIPTION OF THE DRAWINGS

To complete the description being made and in order to aid a better understanding of the characteristics of the invention, according to an example of a preferred embodiment, the description is accompanied by a set of drawings forming an integral part of the description where, for purposes of illustration and in a non-limiting manner, the following is shown.

PREFERRED EMBODIMENT OF THE INVENTION

Figure 1:
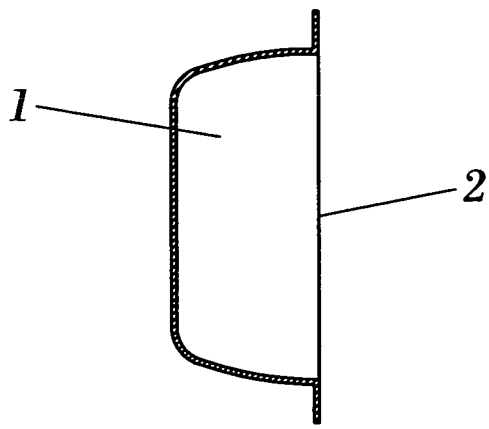
FIG. 1.—Shows a lateral section of the conventional container in the state of the art, showing the membrane deformed when a vacuum is generated inside it as the liquid leaves.
Figure 1:
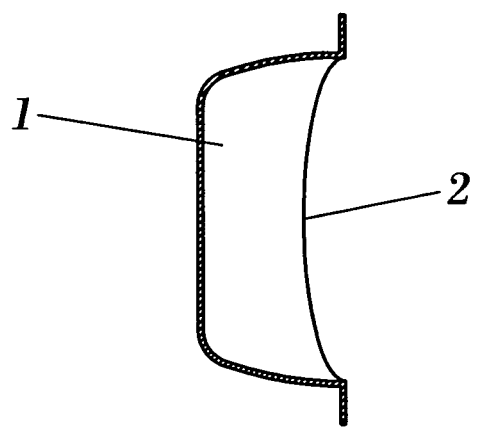
Figure 1:
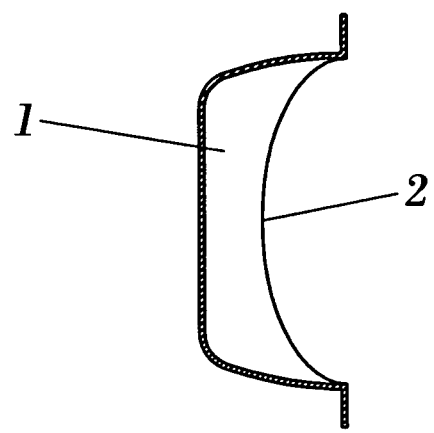
Figure 2:
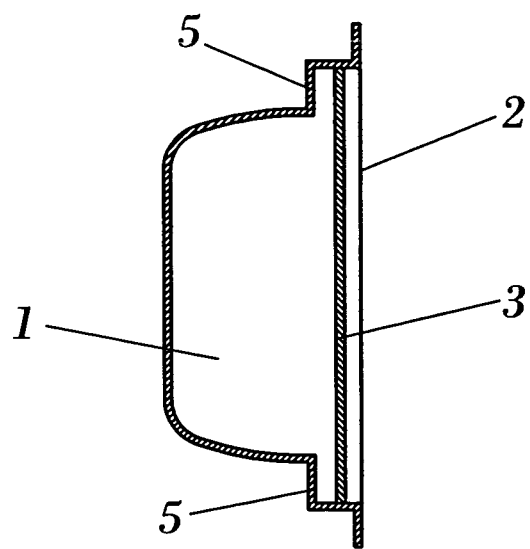
FIG. 2.—Shows a lateral section of the container object of this invention in its normal state and when the membrane is deformed.
Figure 2:
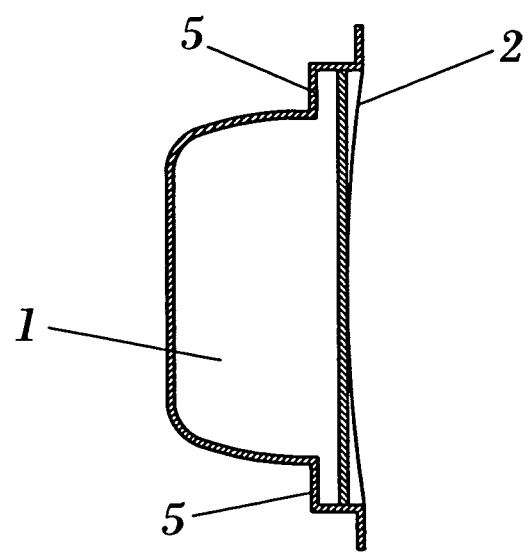
Figure 3:
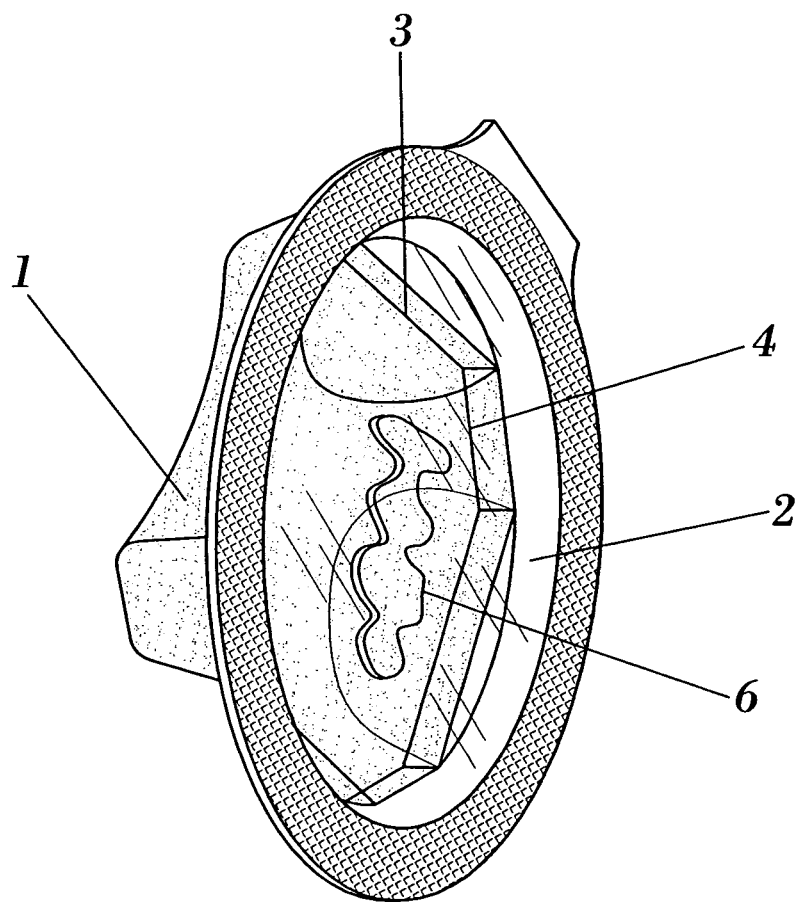
FIG. 3.—Shows a perspective view of a transparent container showing the situation of the porous part inside it.

The container of active substances that constitutes the object of this invention is of the type provided with a vessel (1) that houses the active liquid substance to be diffused, such as a fragrance, insecticide or other, composed of volatile components and non-volatile components, through a breathable membrane (2) that closes the vessel (1) and allows passage of the volatile components in a gaseous state.

With this configuration, the container of active substances mainly stands out in that it comprises a porous part (3) placed near and parallel to the breathable membrane (2) in order to prevent the deformation of the membrane (2) when a vacuum is generated as the vessel (1) is emptied, the porous part (3) also having a number of openings (4) through which passes the liquid to ensure its contact with the membrane (2) at all times for a homogenous evaporation.

The vessel (1) has been designed with a peripheral recess (5) meant to house the porous part (3) that occupies part of the volume of the vessel (1) absorbing the active substances, the non-volatile substances remaining in said porous part (3) after the vessel (1) has no more volatile components.

The vessel (1) may also be transparent and the porous part (3) can include a mark or embossment (6) on its upper or lower face with a commercial drawing or text.

The invention claimed is:

1. A container of active substances comprising:
    a vessel for housing an active liquid substance to be diffused;
    a permeable membrane that closes the vessel and allows passage of volatile components of the active liquid substance in a gaseous state; and
    a porous part placed inside the vessel behind the permeable membrane, wherein the porous part is rigid and is arranged near and parallel to the permeable membrane and spaced apart from the permeable member so that the porous part supports the permeable membrane thereby limiting deformation of the permeable membrane when a vacuum is generated as the vessel is emptied.

2. The container of active substances according to claim 1, wherein the porous part has a number of openings through which the active liquid substance passes to contact the permeable membrane for homogenous evaporation.

3. The container of active substances according to claim 1 or 2, wherein the vessel comprises a peripheral recess to house the porous part that occupies part of the volume of the vessel absorbing the active liquid substances, wherein non-volatile substances of the active liquid substance remain in the porous part after the vessel has no more volatile components of the active liquid substance.

4. The container of active substances according to claim 1 or 2, wherein the vessel is transparent and the porous part comprises an embossment on its upper or lower face.

5. The container according to claim 4, wherein the embossment is a commercial drawing or text.

6. The container according to claim 1 or 2, wherein the active liquid substance is retained within the vessel and the porous part.

7. The container according to claim 1 or 2, wherein the porous part comprises cellulose or porous plastic or a ceramic material.

8. The container according to claim 1 or 2, wherein the active liquid substance comprises a fragrance or an insecticide.

* * * * *